United States Patent [19]

Kochar et al.

[11] 4,334,890
[45] Jun. 15, 1982

[54] PROCESS FOR GASOLINE BLENDING STOCKS

[75] Inventors: Nand K. Kochar, Bronx, N.Y.; Richard L. Marcell, Bergenfield, N.J.

[73] Assignee: The Halcon SD Group, Inc., New York, N.Y.

[21] Appl. No.: 231,205

[22] Filed: Feb. 3, 1981

[51] Int. Cl.³ .............................................. C10L 1/02
[52] U.S. Cl. ..................................... 44/53; 568/697; 568/895; 568/899; 44/56
[58] Field of Search ............... 44/53, 56; 568/895, 568/899, 697

[56] References Cited

U.S. PATENT DOCUMENTS 3,849,082  11/1974  Kozlowski et al. ................... 44/77
3,904,384   9/1975  Kemp et al. ........................... 44/56
3,912,463  10/1975  Kozlowski et al. ................... 44/56

Primary Examiner—Winston A. Douglas
Assistant Examiner—Y. Harris-Smith
Attorney, Agent, or Firm—William C. Long; Riggs T. Stewart; Harold N. Wells

[57] ABSTRACT

A gasoline blending stock is produced by the simultaneous reaction of a hydrocarbon feed containing at least one tertiary olefin, at least one aliphatic alcohol, and water over a suitable catalyst. In a typical embodiment, a mixed $C_4$ stream containing isobutylene is reacted with aqueous ethanol to form a mixture of ethyl tertiary butyl ether and tertiary butanol, with minimal formation of secondary alcohols from any normal butenes present in the hydrocarbon feed.

5 Claims, 1 Drawing Figure

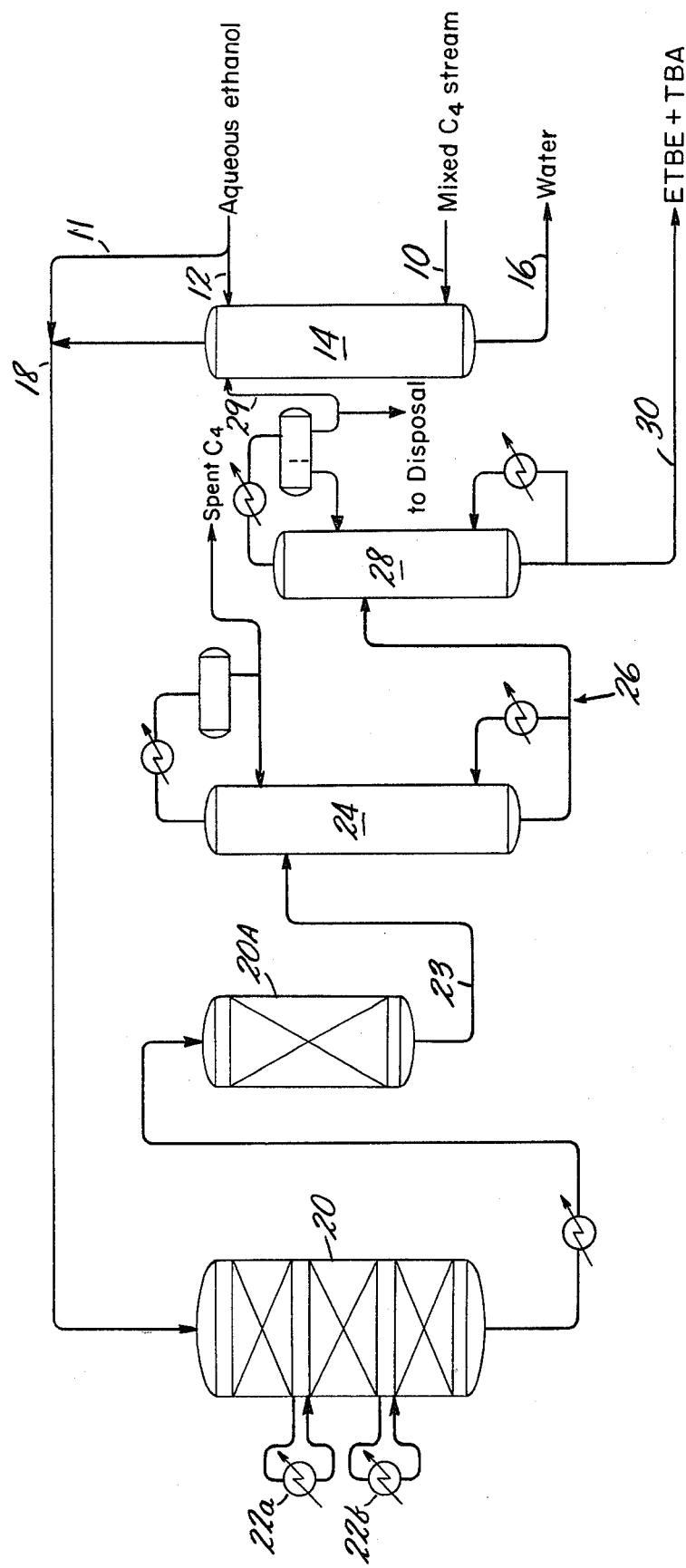

PROCESS FOR GASOLINE BLENDING STOCKS

Prior Art

The invention relates generally to the preparation of gasoline blending stocks such as are commonly used to increase the octane value of gasoline. More specifically, the invention relates to a process for simultaneously producing non-symmetrical alkyl tertiary alkyl ethers and tertiary alcohols, which are useful for blending. In a commercially significant aspect, the invention relates to the reaction of aqueous ethanol with the isobutylene content of a mixed $C_4$ hydrocarbon stream over a suitable catalyst to form a mixture of ethyl tertiary butyl ether (ETBE) and tertiary butanol (TBA).

The reaction of tertiary olefins with alcohols to provide ethers for gasoline blending has been known for many years. Similarly, the hydration of olefins to form the corresponding alcohols is familiar generally to those skilled in the art. Interest in such processes has been revived as increasingly larger amounts of unleaded gasoline have been required. Of particular interest has been methyl tertiary butyl ether (MTBE), which has a particularly high octane value and can be made by reacting isobutylene with methanol over suitable catalysts, particularly acidic ion exchange resins. One of many such processes, for example, is disclosed in U.S. Pat. No. 4,198,530. MTBE has been of particular interest because of the ready availability and the low price of methanol and the high octane number of the gasoline blending stock which is produced.

A recent hydration process for forming tertiary butanol is found in U.S. Pat. No. 4,087,471. In such processes, isobutylene is reacted with water over a suitable catalyst, typically an acidic ion exchange resin, to form tertiary butanol. The discussion in the '471 patent makes clear that the presence of two phases, i.e. water and hydrocarbon, causes difficulties in carrying out the reaction. Consequently, the water added is limited to less than 0.24 mol per mol of isobutene fed, which maintains the reaction product as a single phase. A feature of the process is the recycling a portion of the reactor effluent. Both the normal and tertiary olefins are hydrated to the corresponding alcohols. A number of side reactions occur with significant quantities of isobutene being converted to dimers and heavier compounds. Isomerization of butene-1 to other isomers also is seen to occur.

Typically, one or the other process (i.e. etheration or hydration) would be carried out on a tertiary olefin, but it is known in the art to combine such processes sequentially, as is shown in U.S. Pat. Nos. 3,849,082 and 3,912,463. First, the etheration reaction is carried out by combining methanol and isobutylene to form MTBE with separation of the resulting ether. The residual C4 stream containing normal olefins and paraffinic hydrocarbons is then fed to a hydration reaction where the normal olefins are combined with water to form secondary alcohols (not tertiary alcohols). Again, the alcohol product is separated and the remaining paraffinic hydrocarbons are processed as desired. In U.S. Pat. No. 3,849,082 the isobutane in that stream is partially oxidized to form TBA.

With its high cost relative to methanol and the fact that it is generally produced with a significant water content, ethanol has been given much less attention than methanol in processes by which gasoline blending stocks have been produced. In a recent U.S. Pat. No. 4,207,076 it is shown that aqueous ethanol has certain advantages for gasoline blending when used in combination with ethyl tertiary butyel ether (ETBE). It is shown that solubility of ethanol and water in various gasolines is a significant problem. The "crude ETBE bottoms" used in the examples contains TBA, which might mean that the ETBE was formed in a a reation of isobutylene with aqueous ethanol. However, no specific disclosure of such a process is made.

The present invention comprises a process whereby etheration and hydration are carried out simultaneously over a suitable catalyst to produce a mixture which is capable of being used directly as a gasoline blending stock. Such a process is particularly suited to the reaction of aqueous ethanol with isobutylene, since it obviates the need to dry the ethanol and produces a mixture of compounds suitable for gasoline blending. Since the hydration of olefins is hindered by the relative immiscibility of the water and hydrocarbons (as in U.S. Pat. No. 4,087,471), it has not been clear that the reaction of tertiary olefins with water and an aliphatic alcohol could be carried out simultaneously with satisfactory results. Indeed, one skilled in the art could be seen to prefer a sequential process because process conditions could be selected to suit either etheration or hydration, as shown in U.S. Pat. No. 3,849,082. The advantage for the simultaneous reaction of the invention is not only economic, but also lies in the discovery that under suitable operating conditions for etheration, hydration of tertiary olefins can be carried out and that normal olefins are not hyrated to the corresponding secondary alcohols. Thus, a mixed gasoline blending stock can be produced and normal olefins can be separated for subsequent use for other purposes than gasoline blending. In this respect, in a discussin of a process for producing MTBE, in "Hydrocarbon Processing", Vol. 56, December 1977, p. 99, it is noted that under those conditions that linear butenes are inert and do not form the corresponding ethers. In addition, it is stated that any water present in the feed is reacted to TBA. Of course, in such processes the feed streams are inherently dry and water would be present in only very minor amounts. In contrast, in the present invention the reaction is carried out with aqueous ethanol such as the azeotropic mixture containing about 6 wt% water. The reaction of such relatively large amounts of water with tertiary olefin is an essential aspect of the successful operation of the process of the invention.

With respect to another feature of the present invention, an overall process for the preparation of gasoline blending stocks may comprise a step in which the hydrocarbon feed stream is contacted with aqueous ethanol in order to remove a significant portion of the water present therein while at the same time combining the hydrocarbon feed stream with the ethanol prior to the simultaneous reaction thereof. Of interest with respect to this aspect of the invention is U.S. Pat. No. 2,591,672, which teaches the use of gasoline as an azeotroping agent to prepare a gasoline-alcohol blend.

The distillation of ethanol requires large amounts of energy. However, when the ethanol is not distilled to a high concentration, as in the ethanol-water azeotrope, the energy required can be much reduced. The study by M. Ladisch and K. Dyck reported in Science, August 1979, p. 899 shows that the energy consumption increases rapidly for ethanol concentrations beyond about 85 wt.%. Thus, rejection of water from dilute ethanol-water mixtures without distillation is highly desirable.

SUMMARY OF THE INVENTION

The invention may be broadly described as a process whereby a liquid stream comprising water, at least one aliphatic alcohol, and at least one tertiary olefin is reacted in the presence of a suitable catalyst to produce a mixture of the corresponding tertiary alcohols and alkyl tertiary alkyl ethers. Any normal olefins present are substantially unchanged under the reaction conditions, typically about 30°–90° C. and a pressure sufficient to maintain the reactants in the liquid phase and using suitable catalyst capable of both etheration and hydration, such as acidic ion exchange resins.

In a useful commercial embodiment, a mixed $C_4$ stream, including isobutylene and normal butenes, will be reacted with aqueous ethanol containing 85–95 wt% ethanol in the presence of an acid ion exchange resin catalyst at a temperature of 40°–60° C. and a pressure of about 15 kg/cm$^2$ absolute. The product mixture contains tertiary butanol (TBA) produced by hydration of isobutylene and ethyl tertiary butyl ether (ETBE) produced by the reaction of ethanol and isobutylene. The water is essentially consumed by hydration so that the product is a dry-liquid suitable for use as a gasoline blending stock. Any unreacted ethanol may be retained with the ETBE-TBA mixture or separated for recycle to the reaction.

In another aspect, the invention includes a process in which an aqueous ethanol feed stream is contacted with the hydrocarbon feed stream to provide the ethanol-water-tertiary olefin mixture needed for the reaction, while rejecting excess water as a waste stream.

BRIEF DESCRIPTION OF THE DRAWING

The sole FIGURE shows a flow sheet illustrating a preferred embodiment of the invention.

DESCRIPTION OF THE PREFERRED EMBODIMENTS

Reaction

In a preferred embodiment the process of the invention comprises the simultaneous reaction of water and ethanol with isobutylene in the presence of an acidic cation exchange resin. In a typical commercial embodiment, aqueous ethanol containing about 85–95 wt% ethanol will be reacted with a mixed $C_4$ stream which may contain varying amounts of isobutylene, n-butenes, and butanes, depending upon its source. Typically, a $C_4$ stream derived from stream cracking will contain about 45 mol % isobutylene, 45 mol % normal butenes, and 10 mol % butanes. A $C_4$ stream derived from refinery cat crackers may contain about 15 mol % isobutylene, 35 mol % butenes, and 50 mol % butanes. The invention is, however, not limited to the reaction of isobutylene, but may be applied more generally to hydrocarbon streams containing tertiary olefins which may be reacted with aliphatic alcohols to obtain unsymmetrical alkyl ethers. In the description of the process details which follows, emphasis will be placed on the commercially important reaction of isobutylene with aqueous ethanol, but it will be understood by one skilled in the art that the reaction need not be so limited.

As the process of the invention is applied to a typical mixed $C_4$ stream, the product of such reactions will generally include ethyl tertiary butyl ether (ETBE) and tertiary butanol (TBA) as the primary products. These result from the etheration reaction by which ethanol is reacted with isobutylene and the hydration reaction of isobutylene with water. Both reactions are readily carried out. It appears that ethanol may facilitate the hydration of isobutylene with water by its mutual solubilizing of the reactants. Only minor amounts of by-products such as dimers have been found to be produced at reaction conditions which are favorable to the production of the desired ETBE and TBA. It is a feature of the invention that at the conditions selected for reaction of isobutylene only small amounts of normal butenes are reacted with the water present in order to form secondary alcohols. Although such alcohols would be useful for gasoline blending, they are considered to be of less value than the preferred ETBE and TBA. Moreover, since the normal butenes are not significantly hydrated under the process conditions of the invention, the process provides a convenient means for separating tertiary olefins from a mixed $C_4$ stream and leaving linear olefins which are useful for other purposes, such as production of alkylate, methyl ethyl ketone and butadiene, and others familiar to those skilled in the art.

The reaction will be carried out in the presence of suitable catalysts, particularly the acidic cation exchange resins such as are known to the art and illustrated in the prior art patents earlier mentioned. Examples of suitable catalysts are the following: mineral acids such as sulfuric acid, sulfonated coals, and sulfonated resins and polymers. As shown in the prior art and in the following examples the resin Amberlyst 15 produced by the Rohm & Haas Company is particularly useful for carrying out this reaction.

The resin may be used conveniently as a fixed bed catalyst in a liquid phase reactor. Since the reaction is exothermic, multiple beds may be employed, along with means for cooling the reaction mixture in between the stages. Since the reaction equilibrium favors formation of the desired ether at low temperatures, heat should be removed to maintain the lowest temperature consistent satisfactory reaction rates. The temperature will be typically held below 90° C. in order to prevent the formation of $C_4$ dimers and preferably in the range of 30°–80° C., most preferably between 40°–60° C. The reactor pressure for a mixed $C_4$ stream will be typically about 15 kg/cm$^2$ absolute, which is sufficient to maintain the stream as a liquid during the reaction. It will be understood to those skilled in the art that this pressure may vary depending on the composition of the liquid streams participating in the process.

Alternative types of reactors familiar to those skilled in the art may also be employed. For example, the catalyst may be placed inside tubes which are surrounded by a circulating heat transfer fluid to remove the exothermic heat of reaction. Another possible choice is the use of a diluent along with the reactants which acts as a heat sink and moderates the temperature rise associated with the reaction. The diluent could be used once-through, but usually would be separated from the reaction products, cooled, and recycled to the reactor inlet.

The following examples will illustrate the reaction of the typical mixed $C_4$ stream and compare that reaction with the individual components reacted separately.

EXAMPLE 1

A series of tests was carried out in 75 cc stainless steel bombs to which ethanol, water, isobutylene and Amberlyst 15 were charged. The reaction was carried out for 3 hours at the temperature indicated. The results are shown in Table A.

TABLE A

| Run No. | Temp °C. | Feed Composition, wt % | | | | Conversion, % | | DIB in Product wt % |
| --- | --- | --- | --- | --- | --- | --- | --- | --- |
| | | IB | EtOH | H$_2$O | A-15 | EtOH to ETBE | H$_2$O to TBA | |
| 1 | 40 | 45.1 | 36.6 | — | 18.3 | 97.9 | — | 1.1 |
| 2 | 40 | 51 | 27.8 | 4.9 | 16.3 | 91.0 | 55.2 | 0.12 |
| 3 | 60 | 57.1 | 32.3 | 5.7 | 4.9 | 77.1 | 73.3 | 0.06 |
| 4 | 80 | 58.6 | 31.1 | 5.5 | 4.8 | 87.4 | 70.8 | 0.57 |
| 5 | 100 | 59.8 | 32.6 | 5.7 | 1.9 | 68.4 | 69.7 | 0.61 |

IB = isobutylene
EtOH = ethanol
A-15 = Amberlyst 15
ETBE = ethyl tertiary butyl ether
TBA = tertiary butanol
DIB = isobutylene dimer The results generally indicate the desirability of operating the reaction at as low a temperature as feasible to obtain the highest conversion to ETBE and the least dimer by-product.

Comparing Runs 1 and 2 it can be seen that, whereas essentially all of the isobutylene and ethanol are reacted to form ETBE when no water is present, that when an 85 wt % ethanol is used the water is converted to TBA and the ethanol is converted to ETBE. It also appears that isobutylene dimer is reduced when water is present in the system.

EXAMPLE 2

It appears to be unexpectedly advantageous to hydrate isobutylene in the presence of ethanol, as will be seen from the date presented in Table B. A series of tests were carried out as in Example 1, having in common a reaction temperature of 60° C. for one hour and a catalyst concentration of about 16 wt % of the total charge.

TABLE B

| Run No. | Charge, mol ratios | | Conversion, % | |
| --- | --- | --- | --- | --- |
| | H$_2$O/IB | ETOH/IB | H$_2$O to TBA | ETOH to ETBE |
| 6 | 0.97 | — | 20 | — |
| 7 | — | 0.94 | — | 97 |
| 8 | 0.29 | 0.65 | 52 | 89 |

Comparing runs 6 and 8 it will be seen that the hydration of isobutylene with water alone is quite poor, when ethanol is present, which has a solubilizing effect, the conversion of water to TBA is much greater.

EXAMPLE 3

The extent to which ETBE is formed can be controlled by using excess ethanol to consume all of the isobutylene, as will be seen from the data in Table C. Again, a series of tests were carried out as in Example 1, with a uniform reaction temperature of 60° C. and a catalyst concentration of about 16 wt %.

TABLE C

| Run No. | Charge, mole ratio ETOH/IB | Reaction Time, hr | Conversion of IB, % |
| --- | --- | --- | --- |
| 9 | 0.96 | 1 | 92.6 |
| 10 | 0.96 | 2 | 94.9 |
| 11 | 4.0 | 1 | 98.6 |

EXAMPLE 4

Tests were carried out as in Example 1 except that both isobutylene and normal butenes were included in the feed. The reaction was carried out for one hour at the temperature indicated.

TABLE D

| Run No. | Temp.°C. | Feed Composition, wt % | | | | | |
| --- | --- | --- | --- | --- | --- | --- | --- |
| | | IB | EtOH | H$_2$O | 1-B | 2-B | A-15 |
| 12 | 40 | 31.9 | 18.9 | 2.3 | 16 | 16 | 15 |
| 13 | 60 | 31.9 | 18.9 | 2.3 | 16 | 16 | 15 |

The ratio of isobutylene (IB) to normal butenes (1-B and 2-B) in the feed are both about 2. However, analysis of the product mixture showed that the ratio of secondary butanol to tertiary butanol is 0.0018 at 40° C. and 0.008 at 60° C. The selective reaction of water with the tertiary olefin in preference to the secondary olefin is clearly indicated.

Process Description

The following description is based on the sole FIGURE which illustrates a typical commercial application of the process of the invention when applied to a mixed C$_4$ stream. The mixed C$_4$ stream 10, which typically will contain about 10-45 mol % isobutylene, is combined with an aqueous ethanol stream 12 prior to being introduced into the beds of ion exchange resin catalyst. It is important to the commercial application of the process plants that aqueous ethanol can be used. As is well known, ethanol obtained by fermentation contains substantial amounts of water which must be removed. Since some of this water can be conveniently reacted with isobutylene to form tertiary butanol, the aqueous ethanol stream feed to the reaction may contain as much as about 15-20 wt % water. If a relatively dilute aqueous solution is used, say about 20 wt % water or more, it will be desirable to contact the aqueous ethanol in a countercurrent manner with the mixed C$_4$ feed stream in an extraction column 14 in order to reject excess water (stream 16) while combining ethanol and C$_4$ feed stream.

Typically, ethanol formed by fermentation contains 90-95 wt % water, which is removed by distillation. As previously noted, the energy requirements become much greater as the concentration of ethanol rises above about 85 wt %. Rejection of a portion of the water can be achieved in the process of the invention by contacting the C$_4$ feed stream with aqueous ethanol. One skilled in the art will understand that the extent to which water can be rejected and dilute ethanol can be employed will depend upon many factors, such as the impurities in the fermentation ethanol and their effect on the catalyst used, the composition of the C$_4$ stream, and the cost of carrying out the competing distillation and extraction operations. In the FIGURE, the aqueous ethanol enters the extraction column 14 via line 12. Depending upon such factors as the composition of the ethanol and C$_4$ streams and the amounts of each available it may be desirable to by pass a portion of the aqueous ethanol directly via line 11 to the reactor 20 to optimize the overall process.

The combined stream 18 then is fed to a reactor or to multiple reactors such as 20 and 20A shown in the FIGURE, where ethanol is reacted with isobutylene to form ETBE, while water is also reacted with isobutylene to form TBA, both highly desirable gasoline additives.

Only a very small amount of the normal butenes are hydrated to secondary alcohols or lost to dimers or other by-products. The reaction is illustrated to take place in two reactors (20 & 20A)—the first (20) containing multiple beds with intermediate cooling following by a fourth bed (in reactor 20A) in which the reaction is carried out at the lowest desirable temperature, typically about 40° C. The heat of reaction may also be removed by recirculating a portion of the product after cooling to the inlet of the bed. The mixture leaving the final catalyst bed now contains ETBE, TBA, any excess ethanol which may be present, and unconverted C$_4$'s. This mixture may then be separated in a typical distillation column 24 to separate the unconverted C$_4$'s as a by-product and leaving the higher boiling ether and alcohols to be removed from the bottom of the column 24 and sent (as stream 26) to a finishing column 28 where any light materials and traces of water are removed overhead. The bottoms from the column (stream 30) is a finished gasoline blending stock containing essentially ETBE and TBA, but may contain ethanol if used in excess to assure complete conversion of the isobutylene. Any overhead from the column may be disposed of as desired or recirculated to the reactor 20 via the extraction column 14 by way of line 29, if it contains valuable feed materials.

EXAMPLE 5

A specific description of the process carried out according to the invention and as shown in the sole FIGURE may be given as follows. A commercially available mixed C$_4$ feed stream containing 45 mol % isobutylene, 45 mol % n-butenes, and 10 mol % butanes is fed (10) at a rate of 100 mol/hr into the bottom of the extraction column 14. Passing upwardly, the C$_4$ streams meets a 66 mol/hr ethanol stream (12) containing (as fed to the tower 14) about 70 wt % ethanol, the remainder being water. As the two streams pass countercurrently, excess water is rejected and 22 mol/hr leaves as stream 16 from the bottom of the column for disposal. The combined stream containing about 21.4 mol % ethanol, 9.6 mol % water, 31.2 mol % isobutylene, 31.2 mol % normal butenes, and 6.6 mol % butanes is fed into the first reactor 20 at a temperature of about 50° C. The reacting mixture passes downward to the three beds of ion exchange resin with intermediate cooling being provided between the beds to maintain the temperature within the range of 50°-60° C. Leaving the bottom of the first reactor the stream is cooled to about 35° C. and enters the second reactor 20A, where the reaction is completed. Leaving the second reactor, the stream contains 27.8 mol % ETBE, 9 mol % TBA, 1.4 mol % ETOH, 4 mol % H$_2$O, 5.7 mol % isobutylene, 42.5 mol % normal butenes, 9.4 mol % butanes with less than 0.5 mol % dimer and other by-products. This stream is then fed to a distillation column (24) where the unreacted C$_4$s are separated overhead for further processing. The bottoms (stream 26) from the column contains about 66 mol % ETBE, 21 mol % TBA, and the rest water and ethanol. The stream is then purified in the finishing distillation column 28 to produce at the bottom a gasoline blending stream (30) containing 39 mol/hr of ETBE and TBA. This stream may contain unreacted ethanol as well, if not rejected in column 28 and recycled via line 29 to the extraction column 14 or otherwise disposed of.

What is claimed is:
1. A process for the preparation of a gasoline blending stock comprising a tertiary alcohol and an alkyl tertiary alkyl ether comprising:
(a) reacting a liquid feed stream comprising water, at least one aliphatic alcohol, and at least one tertiary olefin in the presence of a catalyst capable of both etheration and hydration and simultaneously producing a mixture containing the corresponding tertiary alcohols and alkyl tertiary alkyl ethers;
(b) separating the tertiary alcohols and alkyl tertiary alkyl ethers from the mixture produced in (a) to produce a gasoline blending stock.
2. The process of claim 1 wherein said liquid feed stream of (a) is obtained by contacting countercurrently a mixed hydrocarbon stream containing at least one tertiary olefin with an aqueous aliphatic alcohol stream and separating a water stream and said liquid feed stream.
3. The process of claims 1 or 2 wherein said liquid feed stream comprises aqueous ethanol and isobutylene.
4. The process of claims 1 or 2 wherein said reaction is carried out at a temperature within the range of about 30°-90° C. and at a pressure sufficient to maintain the reactants in the liquid phase.
5. The process of claim 3 wherein said reaction is carried out at a temperature within the range of 40°-60° C., and where said aqueous ethanol contains 85-95 wt % ethanol.

* * * * *